US011712272B2

(12) United States Patent
Schwab (10) Patent No.: US 11,712,272 B2
(45) Date of Patent: Aug. 1, 2023

(54) TECHNOLOGIES FOR LINES COUPLED TO SPINES

(71) Applicant: Frank J. Schwab, New York, NY (US)

(72) Inventor: Frank J. Schwab, New York, NY (US)

( * ) Notice: Subject to any disclaimer, the term of this patent is extended or adjusted under 35 U.S.C. 154(b) by 0 days.

(21) Appl. No.: 16/706,151

(22) Filed: Dec. 6, 2019

(65) Prior Publication Data

US 2020/0187993 A1     Jun. 18, 2020

Related U.S. Application Data

(60) Provisional application No. 62/781,030, filed on Dec. 18, 2018.

(51) Int. Cl.
*A61B 17/70*     (2006.01)

(52) U.S. Cl.
CPC ...... *A61B 17/7053* (2013.01); *A61B 17/7091* (2013.01)

(58) Field of Classification Search
CPC ............................................ A61B 17/70–7046
See application file for complete search history.

(56) References Cited

U.S. PATENT DOCUMENTS

| | | | |
|---|---|---|---|
| 5,092,889 A * | 3/1992 | Campbell, Jr. ........ | A61B 17/68 623/23.47 |
| 5,562,660 A * | 10/1996 | Grob ................... | A61B 17/7008 606/250 |
| 6,290,700 B1 * | 9/2001 | Schmotzer ......... | A61B 17/7008 606/263 |
| 6,296,643 B1 | 10/2001 | Hopf ............................... | 606/61 |
| 6,645,211 B2 * | 11/2003 | Magana ............. | A61B 17/7059 606/247 |
| 8,162,993 B2 * | 4/2012 | Ferree ................ | A61B 17/0401 606/228 |
| 8,337,528 B2 * | 12/2012 | Ferree ................ | A61B 17/7053 606/279 |
| 8,454,662 B2 | 6/2013 | Bethell ......................... | 606/263 |
| 8,470,002 B2 | 6/2013 | Allard .......................... | 606/279 |
| 9,220,536 B2 | 12/2015 | Skaggs ......................... | 606/246 |
| 9,770,266 B2 | 9/2017 | Hestad ............... | A61B 17/7022 |
| 9,844,397 B2 | 12/2017 | Carls ............................ | 606/246 |
| 9,949,761 B2 * | 4/2018 | Fening ............... | A61B 17/7022 |
| 2005/0177164 A1 * | 8/2005 | Walters ............... | A61B 17/704 606/86 A |

(Continued)

FOREIGN PATENT DOCUMENTS

| | | |
|---|---|---|
| EP | 2452643 | 9/2013 |
| WO | WO2017201437 A1 | 11/2017 ............. A61B 17/70 |

OTHER PUBLICATIONS

Lowe et al., A posterior tether for fusionless modulation of sagittal plane growth in a sheep model, Spine (Phila Pa 1976). Sep. 1, 2005;30(17 Suppl):S69-74.

(Continued)

*Primary Examiner* — Eduardo C Robert
*Assistant Examiner* — Steven J Cotroneo
(74) *Attorney, Agent, or Firm* — Dentons US LLP (57) ABSTRACT

This disclosure discloses a line coupled to a spine of a user at two points such that the line can be movable relative to those two points. The line can be encased by a protective member between those two points. The line can be covered by a compound between those two points. The line can be guided between those two points.

34 Claims, 8 Drawing Sheets

(56) References Cited

U.S. PATENT DOCUMENTS

| | | | |
|---|---|---|---|
| 2005/0261695 A1 | 11/2005 | Cragg et al. | |
| 2005/0277919 A1 | 12/2005 | Slivka | 606/61 |
| 2006/0149237 A1* | 7/2006 | Markworth | A61B 17/7005 606/279 |
| 2006/0276788 A1* | 12/2006 | Berry | A61B 17/7005 606/286 |
| 2006/0276895 A1* | 12/2006 | Pellegrino | A61B 17/7022 623/13.14 |
| 2007/0129729 A1* | 6/2007 | Petit | A61B 17/7022 606/254 |
| 2007/0288011 A1* | 12/2007 | Logan | A61B 17/7008 606/86 A |
| 2007/0288024 A1* | 12/2007 | Gollogly | A61B 17/68 606/281 |
| 2008/0033436 A1* | 2/2008 | Song | A61B 17/7022 606/86 A |
| 2008/0140123 A1* | 6/2008 | Ferree | A61B 17/7022 606/263 |
| 2008/0234737 A1 | 9/2008 | Boschert | |
| 2008/0255615 A1 | 10/2008 | Vittur | 606/246 |
| 2009/0281574 A1* | 11/2009 | Jackson | A61B 17/7004 606/264 |
| 2009/0281575 A1 | 11/2009 | Carls | |
| 2010/0094302 A1* | 4/2010 | Pool | A61B 17/7004 606/90 |
| 2010/0174319 A1* | 7/2010 | Jackson | A61B 17/7008 606/264 |
| 2010/0217271 A1* | 8/2010 | Pool | A61B 17/707 606/90 |
| 2012/0035661 A1* | 2/2012 | Pool | A61B 17/7016 606/258 |
| 2012/0071928 A1* | 3/2012 | Jackson | A61B 17/7032 606/257 |
| 2012/0143255 A1* | 6/2012 | Jackson | A61B 17/7004 606/259 |
| 2013/0035726 A1 | 2/2013 | Nguyen et al. | |
| 2014/0094854 A1* | 4/2014 | Schwab | A61B 17/7022 606/279 |
| 2014/0358150 A1* | 12/2014 | Kaufman | A61B 17/025 606/90 |
| 2016/0000468 A1 | 1/2016 | Samdani | A61B 17/7022 |
| 2016/0346010 A1* | 12/2016 | Jackson | A61B 17/7005 |
| 2017/0100165 A1 | 4/2017 | Jackson | |
| 2017/0231661 A1 | 8/2017 | Bannigan | A61B 17/7053 |
| 2018/0140327 A1* | 5/2018 | Yue | A61B 17/707 |

OTHER PUBLICATIONS

Skaggs et al., Improvement of Kyphoscoliosis in a 9-Year-Old Using Growth Modulation With a Posterior Tether: A Case Report, Spine Deform. Jan. 2013;1(1):79-83. doi: 10.1016/j.jspd.2012.09.002. Epub Jan. 3, 2013.

Zimmer, Dynesys Top-Loading System Surgical Technique, The Dynamic Stabilization System, https://www.zimmerbiomet.com/content/dam/zimmer-biomet/medical-professionals/000-surgical-techniques/spine/dynesys-top-loading-svstem-surgical-technique.pdf, downloaded from internet Dec. 2019 (44 pages).

Zimmer, The Tether—Vertebral Body Tethering System, https://www.fda.gov/medical-devices/recently-approved-devices/tethertm-vertebral-body-tethering-system-h190005, downloaded from internet Dec. 2019 (3 pages).

International Search Report and Written Opinion dated Apr. 14, 2020 in related International Application No. PCT/US19/66027 filed Dec. 12, 2019 (9 pages).

Europe Office Action dated Mar. 23, 2023 in related Application 19900396.3 filed Dec. 12, 2019 (16 pages).

* cited by examiner

TECHNOLOGIES FOR LINES COUPLED TO SPINES

CROSS-REFERENCE TO RELATED APPLICATIONS

The present patent application claims the benefit of U.S. Provisional Application Ser. No. 62/781,030 filed 18 Dec. 2018, which is incorporated herein by reference in its entirety.

TECHNICAL FIELD

This disclosure relates to lines coupled to spines.

BACKGROUND

There is a desire for a technology to couple a line to a spine for treatment of a medical condition. However, this technology does not exist. Accordingly, this disclosure enables such technology.

SUMMARY

In an embodiment, a device comprises: a first anchor coupled to at least one of a first vertebrae of a spine or a first tissue in proximity to the first vertebrae of the spine; a second anchor coupled to at least one of a second vertebrae of the spine or a second tissue in proximity to the second vertebrae of the spine; a line spanning between the first anchor and the second anchor; and a protective member encasing the line such that the line is movable relative to the protective member between the first anchor and the second anchor.

In an embodiment, a device comprises: a line spanning between a first anchor coupled to at least one of a first vertebrae of a spine or a first tissue in proximity to the first vertebrae of the spine, and a second anchor coupled to at least one of a second vertebrae of the spine or a second tissue in proximity to the second vertebrae of the spine; and a tensioner coupled to the line, wherein the tensioner modifies at least one of a position, a displacement, or a length of the line.

In an embodiment, a device comprises: a line coupled to at least one of a first vertebrae of a spine or a first tissue in proximity to the first vertebrae of the spine, and at least one of a second vertebrae of the spine or a second tissue in proximity to the second vertebrae of the spine; and a compound positioned over the line and at least one of the first vertebrae, the second vertebrae, or a third vertebrae of the spine such that the line is movable within the compound relative to the compound and the at least one of the first vertebrae, the second vertebrae, or the third vertebrae, wherein the third vertebrae is positioned between the first vertebrae and the second vertebrae. In some embodiments, the line is fixed within the compound relative to the compound.

In an embodiment, a device comprises: a first anchor coupled to a first vertebrae of a spine or a first tissue in proximity to the first vertebrae of the spine; a second anchor coupled to a second vertebrae of the spine or a second tissue in proximity to the second vertebrae of the spine; a line spanning between the first anchor and the second anchor; and a guide positioned between the first anchor and the second anchor such that the guide guides the line and such that the line is movable relative to the first anchor and the second anchor.

In some embodiments, the line spans posteriorly between the first anchor and the second anchor. In some embodiments, at least one of the first anchor or the second anchor is coupled to a vertebrae at the posterior of the spine. In some embodiments, the first vertebrae is not adjacent to the second vertebrae. In some embodiments, the first vertebrae is separated from the second vertebrae by a third vertebrae.

DETAILED DESCRIPTION OF PREFERRED EMBODIMENTS

Generally, this disclosure discloses a line coupled to a spine of a user at two points such that the line can be movable between or relative to those two points. The line can be encased or overlaid by a protective member between those two points. The line can be covered by a compound between those two points. The line can be guided between those two points. For example, a method of diagnosing, monitoring, or treating a medical condition of the user can include extending the line from an upper region of the spine to a lower region of the spine based on an anchor anchored at the upper region and an anchor anchored at the lower region, or vice versa. The method of treatment can include positioning a guide along the line such that the guide guides the line and thereby allows the line to remain unimpeded and free moving between or relative to the upper region and the lower region, and/or in multiple dimensions. The line can be encased in a sheath through or within which the line can be moved in one or more dimensions or directions. The sheath can be coupled to the spine using a compound. The compound can be shaped as a tunnel through which the line extends. The line can be tensioned to enable a straightening of the spine. The line can be loosened to enable a forward flexion of the spine. The line can have a force applied thereto, whether positive or negative, or removed, to tension the line or loosen the line. The force can be applied or removed by a tensioner, which in certain embodiments is powered and in some embodiments is adjusted automatically or manually. Once set to a particular tension, the line may bend or flex or be displaced without actually extending or retracting. In some embodiments, the line spans posteriorly between the first anchor and the second anchor. In some embodiments, at least one of the first anchor or the second anchor is coupled to a vertebrae at the posterior of the spine. In some embodiments, the first vertebrae is not adjacent to the second vertebrae. In some embodiments, the first vertebrae is separated from the second vertebrae by a third vertebrae. In some embodiments, the line may be positioned posteriorly to the spine. In some embodiments, the anchors may be coupled such that the line may be positioned posteriorly to the spine. Note that this disclosure may be embodied in many different forms and should not be construed as necessarily being limited to various embodiments disclosed herein. Rather, these embodiments are provided so that this disclosure is thorough and complete, and fully conveys various concepts of this disclosure to skilled artisans.

Note that various terminology used herein can imply direct or indirect, full or partial, temporary or permanent, action or inaction. For example, when an element is referred to as being "on," "connected," or "coupled" to another element, then the element can be directly on, connected, or coupled to another element or intervening elements can be present, including indirect or direct variants. In contrast, when an element is referred to as being "directly connected" or "directly coupled" to another element, then there are no intervening elements present.

As used herein, various singular forms "a," "an" and "the" are intended to include various plural forms as well, unless specific context clearly indicates otherwise.

As used herein, various presence verbs "comprises," "includes" or "comprising," "including" when used in this specification, specify a presence of stated features, integers, steps, operations, elements, or components, but do not preclude the presence or addition of one or more other features, integers, steps, operations, elements, components, or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "or others," "combination", "combinatory," or "combinations thereof" refers to all permutations and combinations of listed items preceding that term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. Skilled artisans understand that typically there is no limit on number of items or terms in any combination, unless otherwise apparent from the context.

As used herein, unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized or overly formal sense unless expressly so defined herein.

As used herein, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" or "substantially" refers to a +/−10% variation from a nominal value/term. Such variation is always included in any given value/term provided herein, whether or not such variation is specifically referred thereto.

Figure 1A:
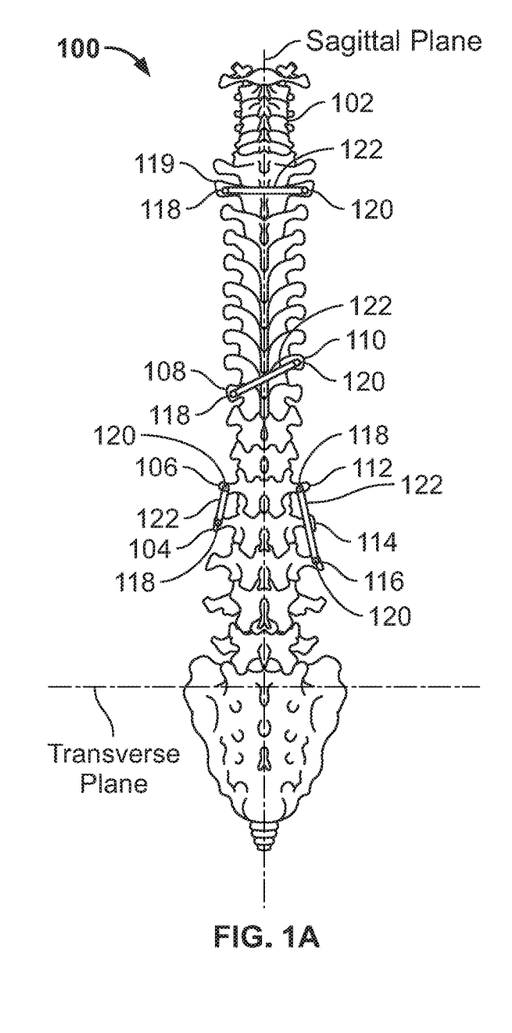
FIG. 1A shows a diagram of an embodiment of a spine having a plurality of lines installed in accordance with this disclosure.
Figure 1B:
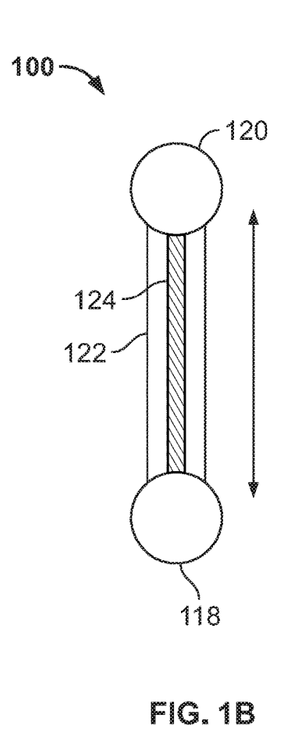
FIG. 1B shows a diagram of an embodiment of a device for installation onto a spine in accordance with this disclosure.
Figure 1C:
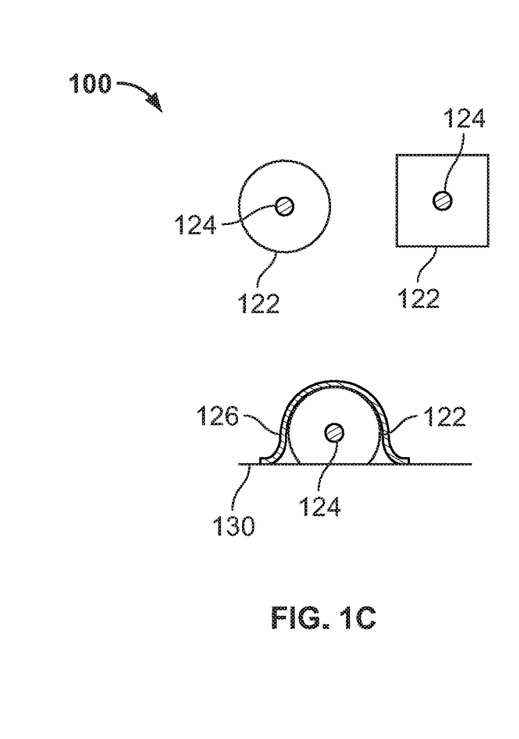
FIG. 1C shows a plurality of diagrams of a plurality of cross-sections of a plurality of embodiments of a plurality of protective members encasing a plurality of lines in accordance with this disclosure.

FIG. 1A shows a diagram of an embodiment of a spine having a plurality of lines installed in accordance with this disclosure. FIG. 1B shows a diagram of an embodiment of a device for installation onto a spine in accordance with this disclosure. FIG. 1C shows a plurality of diagrams of a plurality of cross-sections of a plurality of embodiments of a plurality of protective members encasing a plurality of lines in accordance with this disclosure.

In particular, as shown in FIG. 1A, a spine 100 of a user (e.g., a mammal, an animal, a human) includes a set of vertebrae 102. The set of vertebrae 102 includes a vertebrae 104, a vertebrae 106, a vertebrae 108, a vertebrae 110, a vertebrae 112, a vertebrae 114, a vertebrae 116, and a vertebrae 119, any of which can be or are undergoing a spinal fusion. Note that the set of vertebrae 102 includes the vertebrae 104, the vertebrae 106, the vertebrae 108, the vertebrae 110, the vertebrae 112, a vertebrae 114, the vertebrae 116, the vertebrae 119 for illustrative reasons. Note that this disclosure can be applied to any vertebrae of the spine 100.

A device, as shown in FIG. 1B, includes a first anchor 118, a second anchor 120, a protective member 122, and a line 124. The device can be used to diagnose, monitor, or treat a medical condition. For example, the medical condition can include age related deformity of the spine, scoliosis, kyphosis, flatback, spondylosis, neurodegenerative deformity, trauma related instability or deformity, muscular degeneration, metabolic muscular or bone related pathologies, congenital or idiopathic conditions, iatrogenic pathology, infectious or post-infectious pathology.

The first anchor 118 (e.g., a bone fixation device, a hook, a screw, a wire, an anchor, a dart, a loop) is coupled (e.g., fastening, mating, interlocking, adhering, stapling, tying) to the vertebrae 104 (e.g., a transverse process, spinous process, lamina, pars). The second anchor 120 (e.g., a bone fixation device, a hook, a screw, a wire, an anchor, a dart, a loop) is coupled (e.g., fastening, mating, interlocking, adhering, stapling, tying) to the vertebrae 106 (e.g., a transverse process spinous process, lamina, pars). However, note that the first anchor 118 can be coupled to a tissue (e.g., hard or soft) or an implant in proximity (e.g., about 1 inch or less) to the vertebrae 104. Likewise, note that the second anchor 118 can be coupled to a tissue (e.g., hard or soft) or an implant in proximity (e.g., about 1 inch or less) to the vertebrae 106.

The protective member 122 (e.g., a tube, a sleeve, a partial cylinder, a trough) extends (e.g., spans) between the anchor 118 and the second anchor 120. The protective member 122 can include synthetic material, organic material, metal, plastic, rubber, fabric, or silicon. The protective member 122 can be coupled (e.g., fastening, mating, interlocking, adhering, stapling, tying) to the anchor 118 or the anchor 118. The protective member 122 can be coupled (e.g., fastening, mating, interlocking, adhering, stapling, tying) to the vertebrae 104 or the vertebrae 106. The protective member 122 can be coupled (e.g., fastening, mating, interlocking, adhering, stapling, tying) to a vertebrae other than the vertebrae 104 and the vertebrae 106. The protective member 122 can be coupled (e.g., fastening, mating, interlocking, adhering, stapling, tying) to a hard tissue (e.g., bone) or a soft tissue (e.g., a tendon, a ligament, a skin, a fibrous tissue, a muscle, a nerve, an artery, a vein) or an implant of the user. As shown in FIG. 1C, the protective member 122 can have a cross section that is open-shaped, close-shaped, symmetrical, or asymmetrical (e.g., circular, oval, triangular, pentagonal, octagonal, arcuate, V-shaped, U-shaped, J-shaped, D-shaped, C-shaped, semicircular, curved, flat). The protective member 124 can be solid, semi solid, permeable, or semi-permeable. The protective member 122 can be rigid, semi-rigid, flexible, elastic, or resilient.

The line 124 (e.g., a tether, a cable, a chain, a wire, a rope, a belt, a band, a braid, a tube, a cylinder) extends (e.g., spans) between the anchor 118 and the second anchor 120. The line 124 extends within the protective member 122 such that the protective member 122 encases the line 124 such that the line 124 is movable or displaceable (e.g., longitudinally, laterally, slideably, suspended) within and along the protective member 124 between the anchor 118 and the second anchor 120. The terms "move," "movable," and "movement" include the common meaning of such terms, as well as displace, bend, flex, rotate, shift, displaceable, flexible, rotatable, shiftable, displacement, flexion, rotation, shifting, and includes any or all directions and dimensions, The line 124 can include metal, plastic, rubber, fabric, or silicon. The line 124 can be flat, cylindrical, synthetic, elastic, rigid, woven, or braided. The line 124 can include an autograft or an allograft.

The protective member 122 or the line 124 can extend across a sagittal plane of the user. The protective member 124 or the line 124 can extend along a single vertebrae. The protective member 122 or the line 124 can avoid extending across the sagittal plane of the user.

As shown in FIG. 1C, a compound 126 (e.g., bone cement) can be positioned over the protective member 122 and a vertebrae surface 130 of the spine 100 (e.g. as an arcuate tunnel, a U-shaped tunnel, a C-shaped tunnel, a D-shaped tunnel, an O-shaped tunnel) such that the protective member 122 is coupled (e.g., adhering, bonded) to the vertebrae surface 130 via the compound 126. The vertebrae surface 130 can be the vertebrae 104, the vertebrae 106, or another vertebrae of the spine 100. This other vertebrae can be any vertebrae of the spine 100 and can be positioned between any vertebrae of the set of vertebrae 102.

The line 124 can include a portion coupled to a tensioner (e.g., a pulley, a winch, a spring, a memory metal, a deforming metal, a mechanical movement, a gear, a ratchet, a motor) applying or reducing a tension (e.g., positive, negative) to the line 124. The portion can be an end portion of the line 124 or not an end portion of the line 124. The anchor 118 or the anchor 120 can host (e.g., house, support, encase) the tensioner. The vertebrae 104 or the vertebrae 106 can host (e.g., house, support, encase) the tensioner. The tensioner can be activated (e.g., a magnetic force, an electrical force, a chemical force, or a mechanical force) internal to the user (e.g., wired, wirelessly) or external (e.g., wired, wirelessly) to the user. The tensioner can be positioned internal or external to the user. The tensioner can be manually or automatically activated (e.g., from a smartphone, a wearable, a server), including via a wire, transdermally, or wirelessly.

As shown in FIG. 1A, the protective member 122 or the line 124 can extend along a vertical plane (e.g., along the sagittal plane) and span between the anchor 118 of the vertebrae 104 and the second anchor 120 of the vertebrae 106. In this scenario, the vertebrae 104 and the vertebrae 106 are positioned immediately adjacent to each other and the protective member 122 or the line 124 do not cross the sagittal plane of the user.

Likewise, the protective member 122 or the line 124 can extend along a diagonal plane and span between the anchor 118 of the vertebrae 108 and the second anchor 120 of the vertebrae 110. In this scenario, although the vertebrae 108 and the vertebrae 110 are positioned immediately adjacent to each other, the protective member 122 or the line 124 do cross the sagittal plane of the user.

Similarly, the protective member 122 or the line 124 can extend along a vertical plane (e.g., along the sagittal plane) and span between the anchor 118 of the vertebrae 112 and the second anchor of the vertebrae 116, while the vertebrae 114 is positioned between the vertebrae 112 and the vertebrae 116. In this scenario, the vertebrae 112 and the vertebrae 116 are not positioned immediately adjacent to each other (e.g., due to interpositioning of the vertebrae 114) and the protective member 122 or the line 124 do not cross the sagittal plane of the user. The protective member 122 or the line 124 can contact or avoid contact with the vertebrae 114. The protective member 122 or the line 124 can couple (e.g., fastening, mating, interlocking, adhering, stapling, tying) or avoid coupling to the vertebrae 114.

Additionally, the protective member 122 or the line 124 can extend along a horizontal plane (e.g., along a transverse plane of the user) and span between the anchor 118 of the vertebrae 119 and the second anchor 120 of the vertebrae 119. In this scenario, the protective member 122 or the line 124 are positioned on a common vertebrae and the protective member 122 or the line 124 cross the sagittal plane of the user.

Figure 2A:
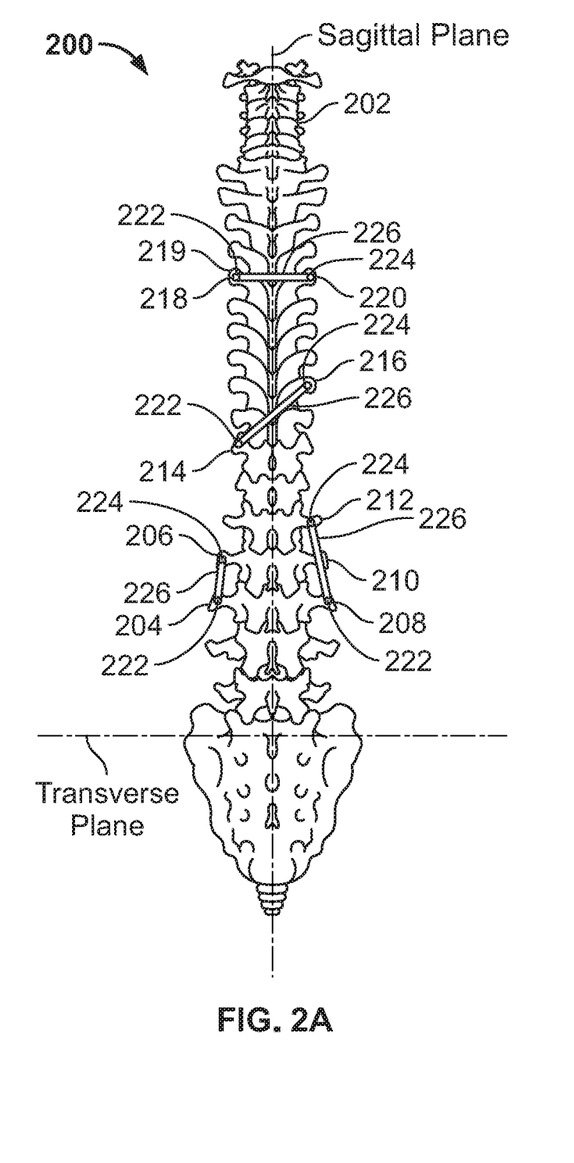
FIG. 2A shows a diagram of an embodiment of a spine having a plurality of lines installed in accordance with this disclosure.
Figure 2B:
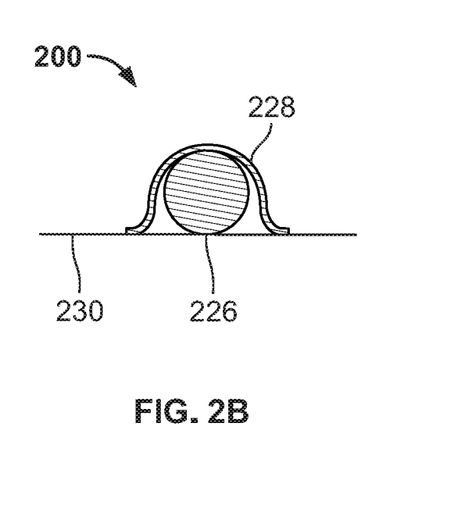
FIG. 2B shows a diagram of an embodiment of a compound positioned over a line in accordance with this disclosure.

FIG. 2A shows a diagram of an embodiment of a spine having a plurality of lines installed in accordance with this disclosure. FIG. 2B shows a diagram of an embodiment of a compound positioned over a line in accordance with this disclosure. In particular, as shown in FIG. 2A, a spine 200 of a user (e.g., a mammal, an animal, a human) includes a set of vertebrae 202. The set of vertebrae 202 includes a vertebrae 204, a vertebrae 206, a vertebrae 208, a vertebrae 210, a vertebrae 212, a vertebrae 214, a vertebrae 216, and a vertebrae 218, any of which can be or are undergoing a spinal fusion. Note that the set of vertebrae 202 includes the vertebrae 204, the vertebrae 206, the vertebrae 208, the vertebrae 210, the vertebrae 212, a vertebrae 214, the vertebrae 216, the vertebrae 218 for illustrative reasons. Note that this disclosure can be applied to any vertebrae of the spine 200.

A device includes a line 226 (e.g., a tether, a cable, a chain, a wire, a rope, a belt, a band, a braid, a tube, a cylinder) and a compound 228 (e.g., bone cement). The device can be used to diagnose, monitor, or treat a medical condition. For example, the medical condition can include age related deformity of the spine, scoliosis, kyphosis, flatback, spondylosis, neurodegenerative deformity, trauma related instability or deformity, muscular degeneration, metabolic muscular or bone related pathologies, congenital or idiopathic conditions, iatrogenic pathology, infectious or post-infectious pathology.

The line 226 is coupled (e.g., secured, tied, adhered, fastened, looped, mated, interlocked) to the vertebrae 204 (e.g., transverse process) via an anchor 222 (e.g., a bone fixation device, a hook, a screw, a wire, an anchor, a dart, a loop) and the vertebrae 206 (e.g., transverse process) via a second anchor 224 (e.g., a bone fixation device, a hook, a screw, a wire, an anchor, a dart, a loop). The compound 228 is positioned over the line 226 and the vertebrae 204, the vertebrae 206, or another vertebrae of the spine 200 (e.g., positioned between the vertebrae 204 and the vertebrae 206) such that the line 226 is coupled (e.g., adhered, bonded) via the compound 228 to the vertebrae 204, the vertebrae 206, or another vertebrae of the spine 200 while the line 226 is movable (e.g., longitudinally, laterally, slideably, suspended) through the compound 228. The line 226 can include metal, plastic, rubber, fabric, or silicon. The line 226 can be flat, cylindrical, synthetic, elastic, rigid, woven, or braided. The line 226 can include an autograft or an allograft. The line 226 can extend or avoid extending across a sagittal plane of the user.

The line 226 can include a portion coupled to a tensioner (e.g., a pulley, a winch, a spring, a memory metal, a deforming metal, a mechanical movement, a gear, a ratchet, a motor) applying or reducing a tension (e.g., positive, negative) to or the length of the line 226. The portion can be an end portion of the line 226 or not an end portion of the line 226. The anchor 222 or the anchor 224 can host (e.g., house, support, encase) the tensioner. The vertebrae 222 or the vertebrae 224 can host (e.g., house, support, encase) the tensioner. The tensioner can be activated (e.g., a magnetic force, an electrical force, a chemical force, or a mechanical force) internal to the user (e.g., wired, wirelessly) or external (e.g., wired, wirelessly) to the user. The tensioner can be positioned internal or external to the user. The tensioner can be manually activated (e.g., from a smartphone, a wearable, a server). The tensioner can be automatically activated (e.g., from a smartphone, a wearable, a server).

A protective member (e.g., a tube, a sleeve, a partial cylinder, a trough) can extend (e.g., spans) between the anchor 222 and the anchor 224. The line 226 extends within the protective member such that the protective member encases the line 226 such that the line 226 is movable (e.g., longitudinally, laterally, slideably, suspended) within and along the protective member between the anchor 222 and the second anchor 224. The protective member can include metal, plastic, rubber, fabric, or silicon. The protective member can be coupled (e.g., fastening, mating, interlocking, adhering, stapling, tying) to the anchor 222 or the second anchor 224. The protective member can be coupled (e.g., fastening, mating, interlocking, adhering, stapling, tying) to the vertebrae 204 or the vertebrae 206. The protective member can be coupled (e.g., fastening, mating, interlocking, adhering, stapling, tying) to a vertebrae other than the vertebrae 204 and the vertebrae 206. The protective member can be coupled (e.g., fastening, mating, interlocking, adhering, stapling, tying) to a hard tissue (e.g., bone) or a soft tissue (e.g., a tendon, a ligament, a skin, a fibrous tissue, a muscle, a nerve, an artery, a vein) or an implant of the user. The protective member can have a cross section that is open-shaped, close-shaped, symmetrical, or asymmetrical (e.g., circular, oval, triangular, pentagonal, octagonal, arcuate, V-shaped, U-shaped, J-shaped, D-shaped, C-shaped, semicircular, curved, flat). The protective member can be solid, semi solid, permeable, or semi-permeable. The protective member can be rigid, semi-rigid, flexible, elastic, or resilient. In certain embodiments, the protective member is not coupled to the vertebrae or anchor or any other artifact, but rather remains freely movable relative to the vertebrae and anchors.

The line 226, the compound 228, or the protective member can extend across a sagittal plane of the user. The line 226, the compound 228, or the protective member can extend along a single vertebrae. The line 226, the compound 228, or the protective member can avoid extending across the sagittal plane of the user.

As shown in FIG. 2A, the line 226, the compound 228, or the protective member can extend along a vertical plane (e.g., along the sagittal plane) and span between the anchor 222 of the vertebrae 204 and the anchor 224 of the vertebrae 206. In this scenario, the vertebrae 204 and the vertebrae 206 are positioned immediately adjacent to each other and the line 226, the compound 228, or the protective member do not cross the sagittal plane of the user.

Likewise, the line 226, the compound 228, or the protective member can extend along a diagonal plane and span between the anchor 222 of the vertebrae 214 and the anchor 224 of the vertebrae 216. In this scenario, although the vertebrae 214 and the vertebrae 216 are not positioned immediately adjacent to each other, the line 226, the compound 228, or the protective member do cross the sagittal plane of the user.

Similarly, the line 226, the compound 228, or the protective member can extend along a vertical plane (e.g., along the sagittal plane) and span between the anchor 222 of the vertebrae 208 and the anchor 224 of the vertebrae 212, while the vertebrae 210 is positioned between the vertebrae 210 and the vertebrae 212. In this scenario, the vertebrae 210 and the vertebrae 212 are not positioned immediately adjacent to each other (e.g., due to interpositioning of the vertebrae 214) and the line 226, the compound 228, or the protective member do not cross the sagittal plane of the user. The line 226, the compound 228, or the protective member can contact or avoid contact with the vertebrae 214. The line 226, the compound 228, or the protective member can couple (e.g., fastening, mating, interlocking, adhering, stapling, tying) or avoid coupling to the vertebrae 214.

Additionally, the line 226, the compound 228, or the protective member can extend along a horizontal plane (e.g., along a transverse plane of the user) and span between the anchor 222 of the vertebrae 218 and the anchor 224 of the vertebrae 218. In this scenario, the line 226, the compound 228, or the protective member are positioned on a common vertebrae and line 226, the compound 228, or the protective member cross the sagittal plane of the user.

Figure 3A:
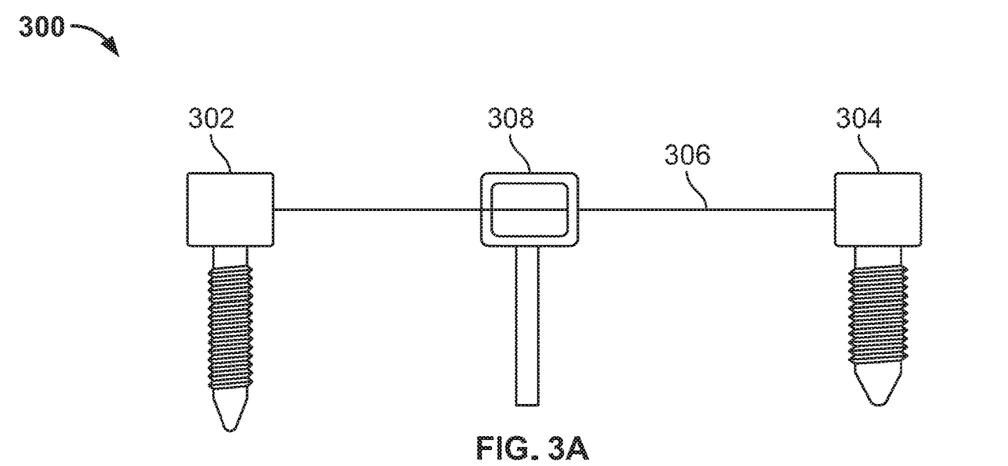
FIG. 3A shows a diagram of an embodiment of a closed-shaped guide guiding a line in accordance with this disclosure.
Figure 3B:
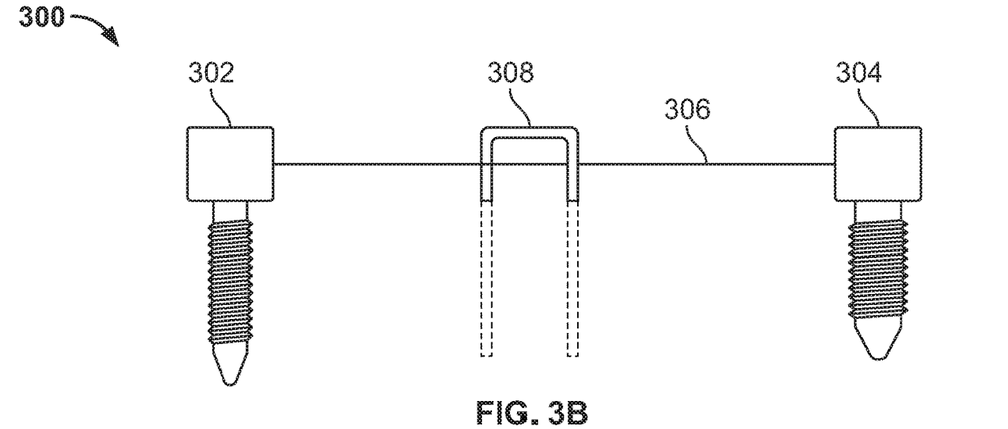
FIG. 3B shows a diagram of an embodiment of a U-shaped guide guiding a line in accordance with this disclosure.
Figure 3C:
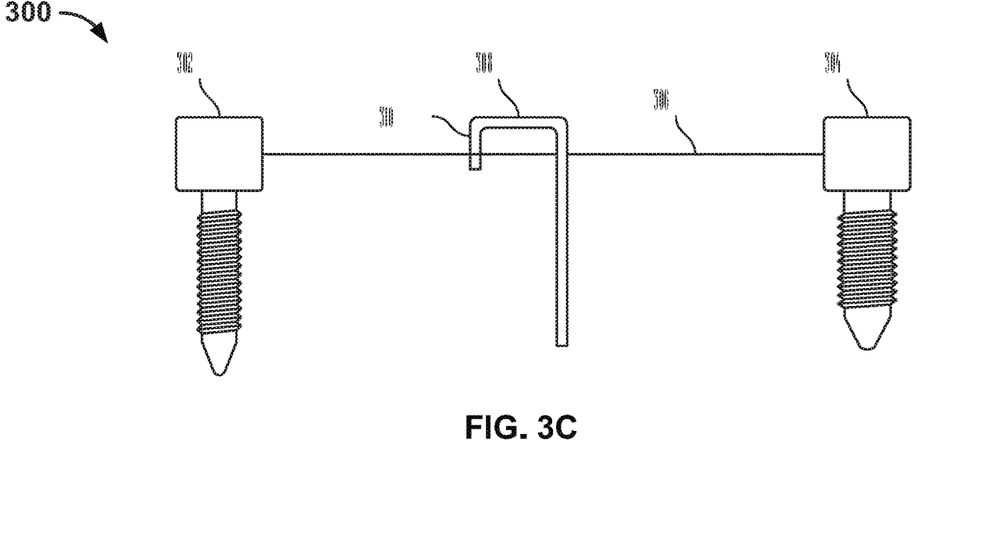
FIG. 3C shows a diagram of an embodiment of an open-shaped guide guiding a line in accordance with this disclosure.

FIG. 3A shows a diagram of an embodiment of a closed-shaped guide guiding a line in accordance with this disclosure. FIG. 3B shows a diagram of an embodiment of a U-shaped guide guiding a line in accordance with this disclosure. FIG. 3C shows a diagram of an embodiment of an open-shaped guide guiding a line in accordance with this disclosure. In particular, a guide system 300 includes a bone screw 302, a bone screw 304, a line 306 (e.g., a tether, a cable, a chain, a wire, a rope, a belt, a band, a braid, a tube, a cylinder), and a guide 308.

The bone screw 302 can be coupled (e.g., fastened, adhered, mated) to a first vertebrae of a spine of a user (e.g., a mammal, an animal, a human) and the bone screw 304 can be coupled (e.g., fastened, adhered, mated) to a second vertebrae of the spine of the user. Note that the bone screw 302 and the bone screw 304 are illustrative and other anchors are possible (e.g., a bone fixation device, a hook, a wire, an anchor, a dart, a loop). Alternatively, the bone screw 302 and/or 304 may be coupled to one or more ribs. Alternatively, there may be used a tissue anchor in place of the bone screw 302 and/or the bone screw 304. In one or more embodiments, there is a third vertebrae positioned between the first vertebrae and the second vertebrae.

The line 306 can include metal, plastic, rubber, fabric, or silicon. The line 306 can be flat, cylindrical, synthetic, elastic, rigid, woven, or braided. The line 306 can include an autograft or an allograft. The line 306 can extend or avoid extending across a sagittal plane of the user. The line 306 can extend posteriorly to the spine. The line 306 can include a portion coupled to a tensioner (e.g., a pulley, a winch, a spring, a memory metal, a deforming metal, a mechanical movement, a gear, a ratchet, a motor) applying or reducing a tension (e.g., positive, negative) to the line 306. The portion can be an end portion of the line 306 or not an end portion of the line 306. The bone screw 302 or the bone screw 304 can host (e.g., house, support, encase) the tensioner. The first vertebrae or the vertebrae can host (e.g., house, support, encase) the tensioner. The tensioner can be activated (e.g., a magnetic force, an electrical force, a chemical force, or a mechanical force) internal to the user (e.g., wired, wirelessly) or external (e.g., wired, wirelessly) to the user. The tensioner can be positioned internal or external to the user. The tensioner can be manually activated (e.g., from a smartphone, a wearable, a server). The tensioner can be automatically activated (e.g., from a smartphone, a wearable, a server).

The guide 308 is positioned between the bone screw 302 and the bone screw 304 such that the guide 308 guides the line 306 and such that the line 306 is movable between or relative to the bone screw 302 and the bone screw 304. The guide 308 can include plastic, metal, rubber, or silicon. The guide 308 can apply a constraint to the line 306 such that the line 306 is movable based on the constraint. The guide 308 can direct a displacement of the line 306 relative to the first vertebrae or the second vertebrae. The guide 308 can reduce an unwanted displacement of the line 306 relative to the first vertebrae or the second vertebrae. The guide 308 can include an open-shaped section (e.g., U-shape, C-shape, V-shape, J-shape, L-shape) or a closed-shaped section (e.g., polygon, O-shape, D-shape, square, rectangle, circle, oval, ellipse, pentagon, octagon, triangle, star), including in the form of a loop, guiding the line 306. The guide 308 can be coupled (e.g., fastened, interlocked, mated, adhered, bonded, stapled, tied, looped) to a vertebrae of the spine (e.g., the first vertebrae, the second vertebrae, another vertebrae), a hard tissue (e.g., bone), or a soft tissue (e.g., a tendon, a ligament, a skin, a fibrous tissue, a muscle, a nerve, an artery, a vein) or an implant. The guide 308, the first vertebrae, and the second vertebrae can be positioned on a common side of the sagittal plane or be distributed on both sides of the sagittal plane. The guide 308 can be the tensioner.

A protective member (e.g., a tube, a sleeve, a partial cylinder, a trough) can extend (e.g., spans) between the bone screw 302 and the bone screw 304. The line 306 can extend within the protective member such that the protective member encases the line 306 such that the line 306 is movable (e.g., longitudinally, laterally, slideably, suspended) within and/or along the protective member between the bone screw 302 and the bone screw 304. The protective member can include metal, plastic, rubber, fabric, or silicon. The protective member can be coupled (e.g., fastening, mating, interlocking, adhering, stapling, tying) to the bone screw 302 or the bone screw 304. The protective member can be coupled (e.g., fastening, mating, interlocking, adhering, stapling, tying) to the first vertebrae or the second vertebrae. The protective member can be coupled (e.g., fastening, mating, interlocking, adhering, stapling, tying) to a vertebrae other than the first vertebrae and the second vertebrae. The protective member can be coupled (e.g., fastening, mating, interlocking, adhering, stapling, tying) to a hard tissue (e.g., bone) or a soft tissue (e.g., a tendon, a ligament, a skin, a fibrous tissue, a muscle, a nerve, an artery, a vein) or an implant of the user. The protective member can be uncoupled from all artifacts. The protective member can have a cross section that is open-shaped, close-shaped, symmetrical, or asymmetrical (e.g., circular, oval, triangular, pentagonal, octagonal, arcuate, V-shaped, U-shaped, J-shaped, D-shaped, C-shaped, semicircular, curved, flat). The protective member can be solid, semi solid, permeable, or semi-permeable. The protective member can be rigid, semi-rigid, flexible, elastic, or resilient. The protective member can couple to the guide 308 (e.g., fastening, mating, interlocking, adhering, magnetizing, bonding). A compound (e.g., bone cement, glue, polymer) can be positioned over the protective member and a vertebrae surface of the spine (e.g., as an arcuate tunnel, a U-shaped tunnel, a C-shaped tunnel, a D-shaped tunnel, an O-shaped tunnel) such that the protective member is coupled (e.g., adhering, bonded, attached) to the vertebrae surface via the compound.

As shown in FIG. 3A, the guide 308 is shaped as an eyelet (e.g., O-shape, D-shape) and a stem, with the stem supporting the eyelet (e.g., monolithic, assembly). The line 306 extends through the eyelet. Similarly, as shown in FIG. 3B, the guide 308 is shaped as a U-shape or C-shape staple (e.g., titanium, stainless steel) that is stapled into a tissue (e.g., hard, soft) or an implant. The line 306 extends an open area within the U-shaped or the C-shaped staple. Likewise, in FIG. 3C, the guide 308 is shaped as a J-shape or an L-shape with a tail 310. The line 306 extends through an open area within the J-shape or the L-shape such that the tail 310 effectively prevents the line 306 from being unguided by the guide 308.

Figure 4:
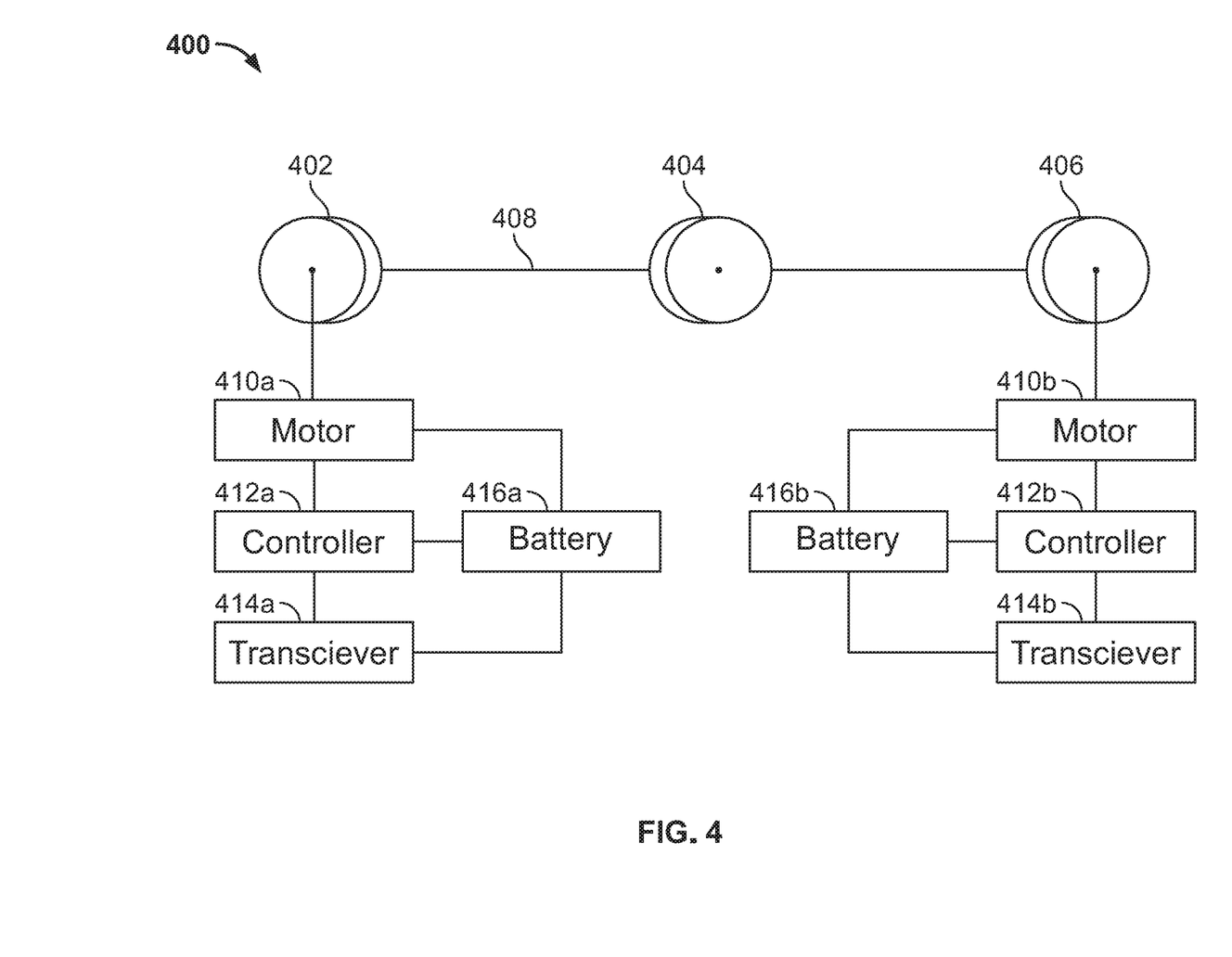
FIG. 4 shows a diagram of an embodiment of a tensioner system for applying a tension to a line in accordance with this disclosure.

FIG. 4 shows a diagram of an embodiment of a tensioner system for applying or reducing a tension to a line in accordance with this disclosure. In certain embodiments, the length of the line is adjusted to modify the tension. In particular, a tensioner system 400 includes a pulley wheel 402, a pulley wheel 404, a pulley wheel 406, a line 408, a motor 410A, a controller 412A, a transceiver 414A, a battery 416A, a motor 410B, a controller 412B, a transceiver 414B, and a battery 416B. The tensioner system 400 can be used to diagnose, monitor, or treat a medical condition. For example, the medical condition can include age related deformity of the spine, scoliosis, kyphosis, flatback, spondylosis, neurodegenerative deformity, trauma related instability or deformity, muscular degeneration, metabolic muscular or bone related pathologies, congenital or idiopathic conditions, iatrogenic pathology, infectious or post-infectious pathology.

The pulley wheel 402 (e.g., round, square, oval, triangle, symmetrical, asymmetrical) is mounted on an axle (e.g., rectilinear bar, arcuate shaft) that is designed to support a movement or a change of direction of the line 408. The axle can be coupled to a platform (e.g., U-shape, C-shape, H-shape) or be a part of the platform. The pulley wheel 402 can have a groove between a pair of flanges around its circumference/perimeter to locate the line 408. Via the platform, the pulley wheel 402 can be coupled (e.g., fastened, mated, interlocked, adhered) to a tissue (e.g., hard, soft), such as a vertebrae of a spine of a user (e.g., single vertebrae, multiple vertebrae, adjacent vertebrae, non-adjacent vertebrae) or an implant of the user. The pulley wheel 402 can be internal (e.g., locally implanted) or external (e.g., held, worn) to the user.

The pulley wheel 404 (e.g., round, square, oval, triangle, symmetrical, asymmetrical) is mounted on an axle (e.g., rectilinear bar, arcuate shaft) that is designed to support a movement or a change of direction of the line 408. The axle can be coupled to a platform (e.g., U-shape, C-shape, H-shape) or be a part of the platform. The pulley wheel 404 can have a groove between a pair of flanges around its circumference/perimeter to locate the line 408. Via the platform, the pulley wheel 404 can be coupled (e.g., fastened, mated, interlocked, adhered) to a tissue (e.g., hard, soft), such as a vertebrae of the spine of the user (e.g., single vertebrae, multiple vertebrae, adjacent vertebrae, non-adjacent vertebrae) or an implant. The pulley wheel 404 (and all of its components) can be identical to or non-identical to the pulley wheel 402 (and all of its components). The pulley wheel 404 can be internal (e.g., locally implanted) or external (e.g., held, worn) to the user.

The pulley wheel 406 (e.g., round, square, oval, triangle, symmetrical, asymmetrical) is mounted on an axle (e.g., rectilinear bar, arcuate shaft) that is designed to support a movement or a change of direction of the line 408. The axle can be coupled to a platform (e.g., U-shape, C-shape, H-shape) or be a part of the platform. The pulley wheel 406 can have a groove between a pair of flanges around its circumference/perimeter to locate the line 408. Via the platform, the pulley wheel 406 can be coupled (e.g., fastened, mated, interlocked, adhered) to a tissue (e.g., hard, soft), such as a vertebrae of the spine of the user (e.g., single vertebrae, multiple vertebrae, adjacent vertebrae, non-adjacent vertebrae) or an implant. The pulley wheel 406 (and all of its components) can be identical to or non-identical to the pulley wheel 402 (and all of its components) or the pulley wheel 404 (and all of its components). The pulley wheel 406 can be internal (e.g., locally implanted) or external (e.g., held, worn) to the user.

The pulley wheel 404 is positioned between the pulley wheel 402 and the pulley wheel 406. The pulley wheel 402, the pulley wheel 404, or the pulley wheel 406 can be omitted. Note that less than three pulley wheels are possible (e.g., at least one) or more than three pulley wheels are possible (e.g., at least four).

The line 408 (e.g., a tether, a cable, a chain, a wire, a rope, a belt, a band, a braid, a tube, a cylinder) can include metal, plastic, rubber, fabric, or silicon, or other organic or inorganic materials. The line 408 can be flat, cylindrical, synthetic, elastic, rigid, woven, or braided. The line 408 can include an autograft or an allograft. The line 408 can extend or avoid extending across a sagittal plane of the user. The line 408 can be coupled (e.g., fastened, interlocked, mated, adhered, tied, looped, bonded) to the pulley wheel 402. The line 408 can be coupled (e.g., fastened, interlocked, mated, adhered, tied, looped, bonded) to the pulley wheel 406. Note that the pulley wheel 402, the pulley wheel 404, or the pulley wheel 406 can be engaging (e.g., meshing) with another pulley wheel such that the line 408 can be positioned (e.g., interposed) therebetween. The pulley wheel 404 supports or guides the line 408 between the pulley wheel 402 and the pulley wheel 406. The pulley wheel 404 can be omitted.

A protective member (e.g., a tube, a sleeve, a partial cylinder, a trough) can extend (e.g., spans) between the pulley wheel 402 and the pulley wheel 406. The line 408 can extend within the protective member such that the protective member encases the line 406 such that the line is movable (e.g., longitudinally, laterally, slideably, suspended) within, along, or relative to the protective member between the pulley wheel 402 and the pulley wheel 406. The protective member can include metal, plastic, rubber, fabric, or silicon. The protective member can be coupled (e.g., fastening, mating, interlocking, adhering, stapling, tying) to the pulley wheel 402 or the pulley wheel 406, while still enabling pulley wheel 402 or the pulley wheel 406 to rotate. The protective member can be coupled (e.g., fastening, mating, interlocking, adhering, stapling, tying) to a vertebrae of the spine of the user. The protective member can be coupled (e.g., fastening, mating, interlocking, adhering, stapling, tying) to a hard tissue (e.g., bone) or a soft tissue (e.g., a tendon, a ligament, a skin, a fibrous tissue, a muscle, a nerve, an artery, a vein) or an implant of the user. The protective member can have a cross section that is open-shaped, close-shaped, symmetrical, or asymmetrical (e.g., circular, oval, triangular, pentagonal, octagonal, arcuate, V-shaped, U-shaped, J-shaped, D-shaped, C-shaped, semicircular, curved, flat). The protective member can be solid, semi solid, permeable, or semi-permeable. The protective member can be rigid, semi-rigid, flexible, elastic, or resilient. The protective member can couple to a guide (e.g., fastening, mating, interlocking, adhering, magnetizing, bonding). The guide can be positioned between the pulley wheel 402 and the pulley wheel 406. A compound (e.g., bone cement) can be positioned over the protective member and a vertebrae surface of the spine (e.g., as an arcuate tunnel, a U-shaped tunnel, a C-shaped tunnel, a D-shaped tunnel, an O-shaped tunnel) such that the protective member is coupled (e.g., adhering, bonded) to the vertebrae surface via the compound.

The motor 410A (e.g., brushed, brushless) can be coupled (e.g., a gear system, a common axle) to the axle of the pulley wheel 402. The motor 410A can be powered (e.g., via a wire, a solid conductor) via the battery 416A (e.g., rechargeable, non-rechargeable). The motor 410A can be controlled (e.g. on, activate, off, deactivate, increase rotational speed, decrease rotational speed) via the controller 412A (e.g., a processor, a logic circuit). The controller 412A is powered (e.g., via a wire, a solid conductor) via the battery 416A. The controller 412A controls (e.g., on, activate, off, deactivate, receive or send messages) the transceiver 414A. The transceiver 414A is powered (e.g., via a wire, a solid conductor) via the battery 416A. The transceiver 414A can communicate in a wired or a wireless manner (e.g., a radio wave, a light wave, a sound wave) with a communication device (e.g., a housing, a case, a smartphone, a tablet, a wearable, a laptop, a desktop), whether the communication device is internal (e.g., locally implanted) or external (e.g., held, worn, remote) to the user. The communication device can communicate with the transceiver 414A based on a manual input thereinto (e.g., user interface) or as preprogrammed (e.g., follow schedule, threshold satisfaction or non-satisfaction).

The motor 410B (e.g., brushed, brushless) can be coupled (e.g., a gear system, a common axle) to the axle of the pulley wheel 406. The motor 410A and the motor 410B can be identical or non-identical to each other. The motor 410B can be powered (e.g., via a wire, a solid conductor) via the battery 416B (e.g., rechargeable, non-rechargeable). The battery 416A and the battery 416B can be identical or non-identical to each other. The motor 410B can be controlled (e.g., on, activate, off, deactivate, increase rotational speed, decrease rotational speed) via the controller 412B (e.g., a processor, a logic circuit). The controller 412A and the controller 412B can be identical or non-identical to each other. The controller 412B is powered (e.g., via a wire, a solid conductor) via the battery 416B. The controller 412B controls (e.g., on, activate, off, deactivate, receive or send messages) the transceiver 414B. The transceiver 414A and the transceiver 414B can be identical or non-identical to each other. The transceiver 414B is powered (e.g., via a wire, a solid conductor) via the battery 416B. The transceiver 414B can communicate in a wired or a wireless manner (e.g., a radio wave, a light wave, a sound wave) with a communication device (e.g., a housing, a case, a smartphone, a tablet, a wearable, a laptop, a desktop), whether the communication device is internal (e.g., locally implanted) or external (e.g., held, worn, remote) to the user. The communication device can communicate with the transceiver 414B based on a manual input thereinto (e.g., mechanical user interface, virtual user interface) or as preprogrammed (e.g., follow schedule, threshold satisfaction or non-satisfaction). The communication device in communication with the transceiver 414A can be identical or non-identical to the communication device in communication with the transceiver 414B. Note that the pulley wheel 404 can be driven similar to the pulley wheel 402 or the pulley wheel 406.

Figure 5:
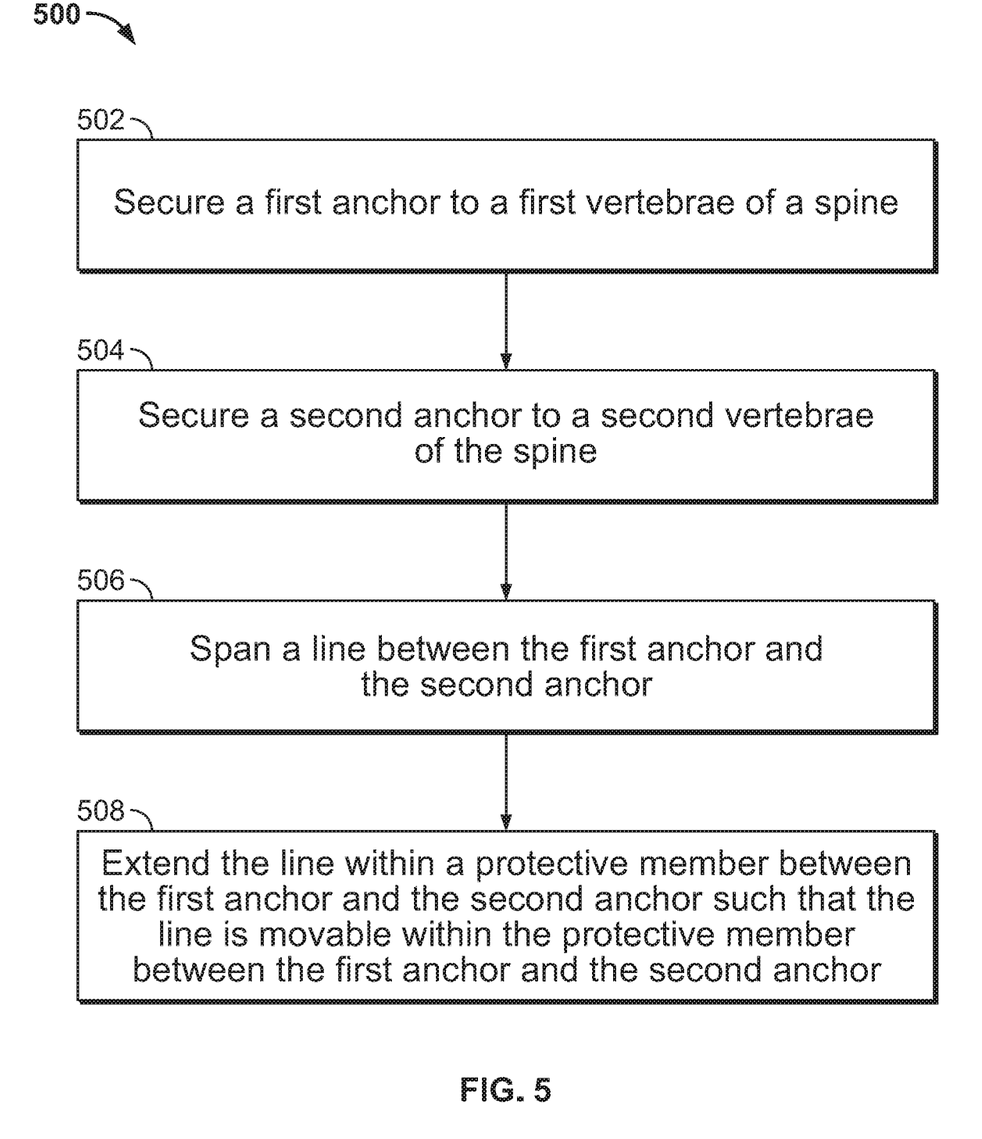
FIG. 5 shows a flowchart for an embodiment of a process to extend a line within a protective member in accordance with this disclosure.

FIG. 5 shows a flowchart for an embodiment of a process to extend a line within a protective member in accordance with this disclosure. In particular, a process 500 includes a plurality of blocks 502-508. In block 502, a first anchor is secured to a first vertebrae of a spine, as disclosed herein. In block 504, a second anchor is secured to a second vertebrae of the spine, as disclosed herein. In block 506, a line is spanned between the first anchor and the second anchor, as disclosed herein. In block 508, the line is extended within a protective member between the first anchor and the second anchor such that the line is movable within or relative to the protective member between the first anchor and the second anchor, as disclosed herein. Note that the block 508 can precede the block 506 or the block 504 or the block 502. In some embodiments, the line spans posteriorly between the first anchor and the second anchor, and within the protective member. In some embodiments, at least one of the first anchor or the second anchor is coupled to a vertebrae at the posterior of the spine. In some embodiments, the first vertebrae is not adjacent to the second vertebrae. In some embodiments, the first vertebrae is separated from the second vertebrae by a third vertebrae.

Figure 6:
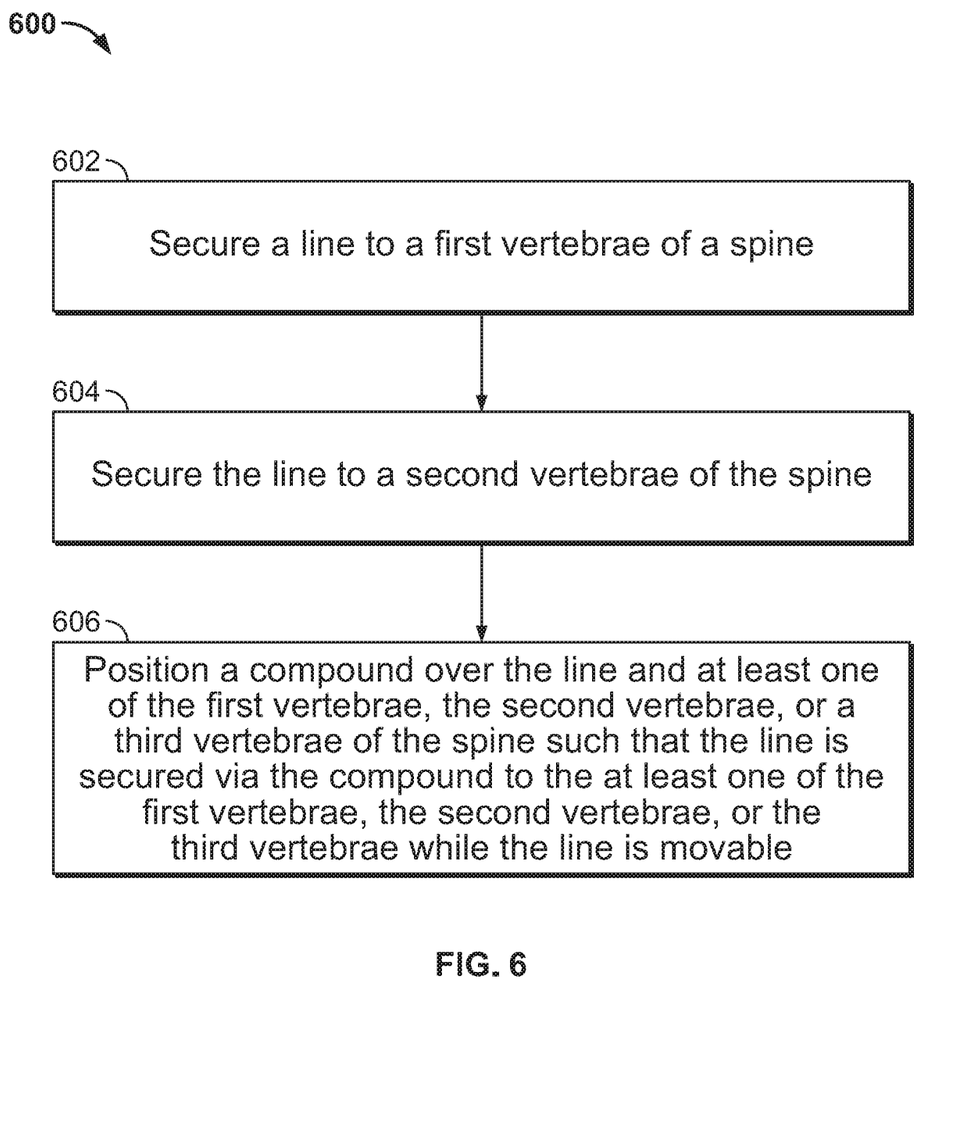
FIG. 6 shows a flowchart for an embodiment of a process to position a compound of a line in accordance with this disclosure.

FIG. 6 shows a flowchart for an embodiment of a process to position a compound of a line in accordance with this disclosure. In particular, a process 600 includes a plurality of blocks 602-606. In block 602, a line is secured to a first vertebrae of a spine, as disclosed herein. In block 604, the line is secured to a second vertebrae of the spine, as disclosed herein. In block 606, a compound is positioned over the line and at least one of the first vertebrae, the second vertebrae, or a third vertebrae of the spine such that the line is secured via the compound to the at least one of the first vertebrae, the second vertebrae, or the third vertebrae while the line is movable, as disclosed herein. Note that the block 606 can precede the block 602 or the block 604.

Figure 7:
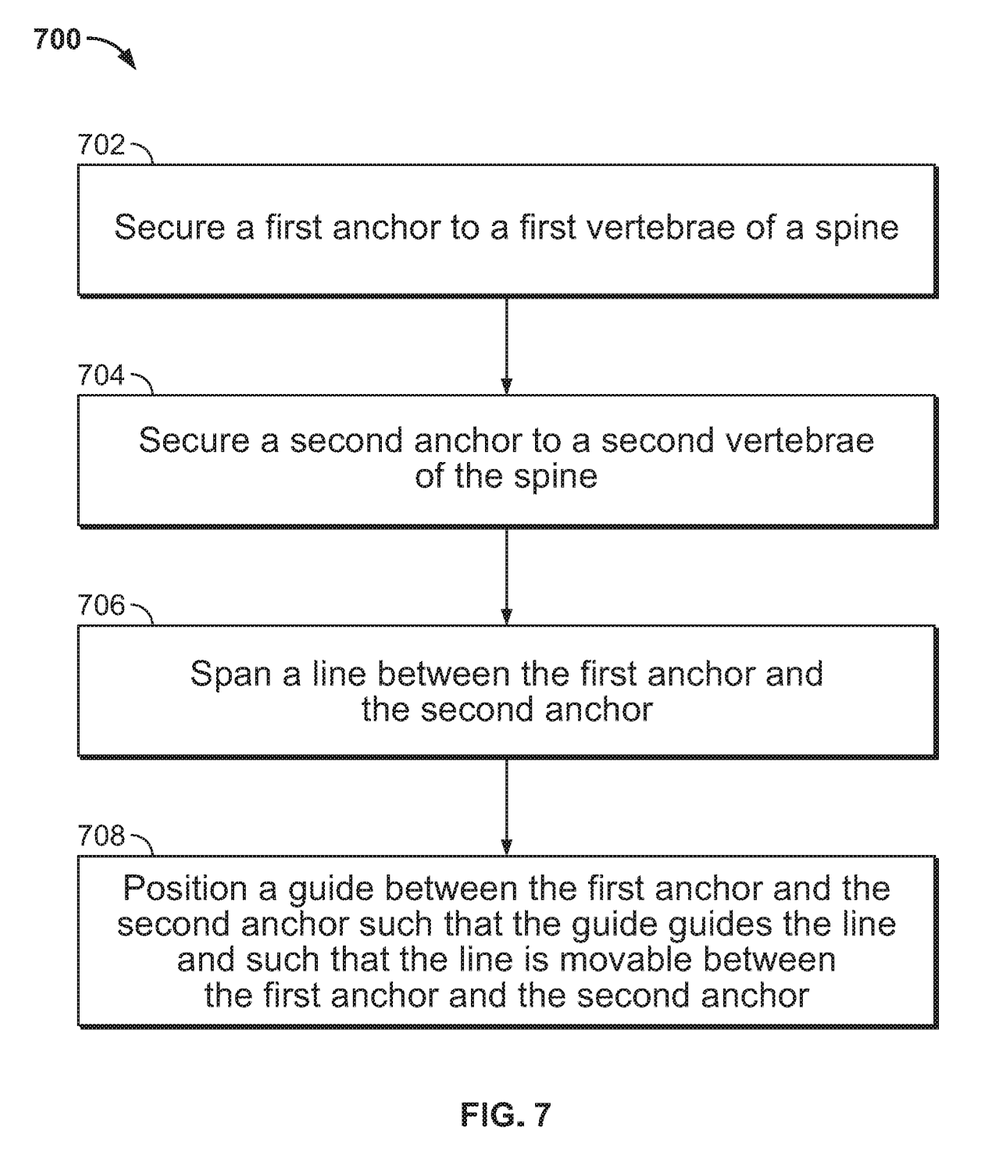
FIG. 7 shows a flowchart for an embodiment of a process to guide a line in accordance with this disclosure.

FIG. 7 shows a flowchart for an embodiment of a process to guide a line in accordance with this disclosure. In particular, a process 700 includes a plurality of blocks 702-708. In block 702, a first anchor is secured to a first vertebrae of a spine, as disclosed herein. In block 704, the second anchor is secured to a second vertebrae of the spine, as disclosed herein. In block 706, a line is spanned between the first anchor and the second anchor, as disclosed herein. In block 706, a guide is positioned between the first anchor and the second anchor such that the guide guides the line and such that the line is movable between or relative to the first anchor and the second anchor, as disclosed herein. Note that the block 708 can precede the block 706, the block 704, or the block 702.

Figure 8:
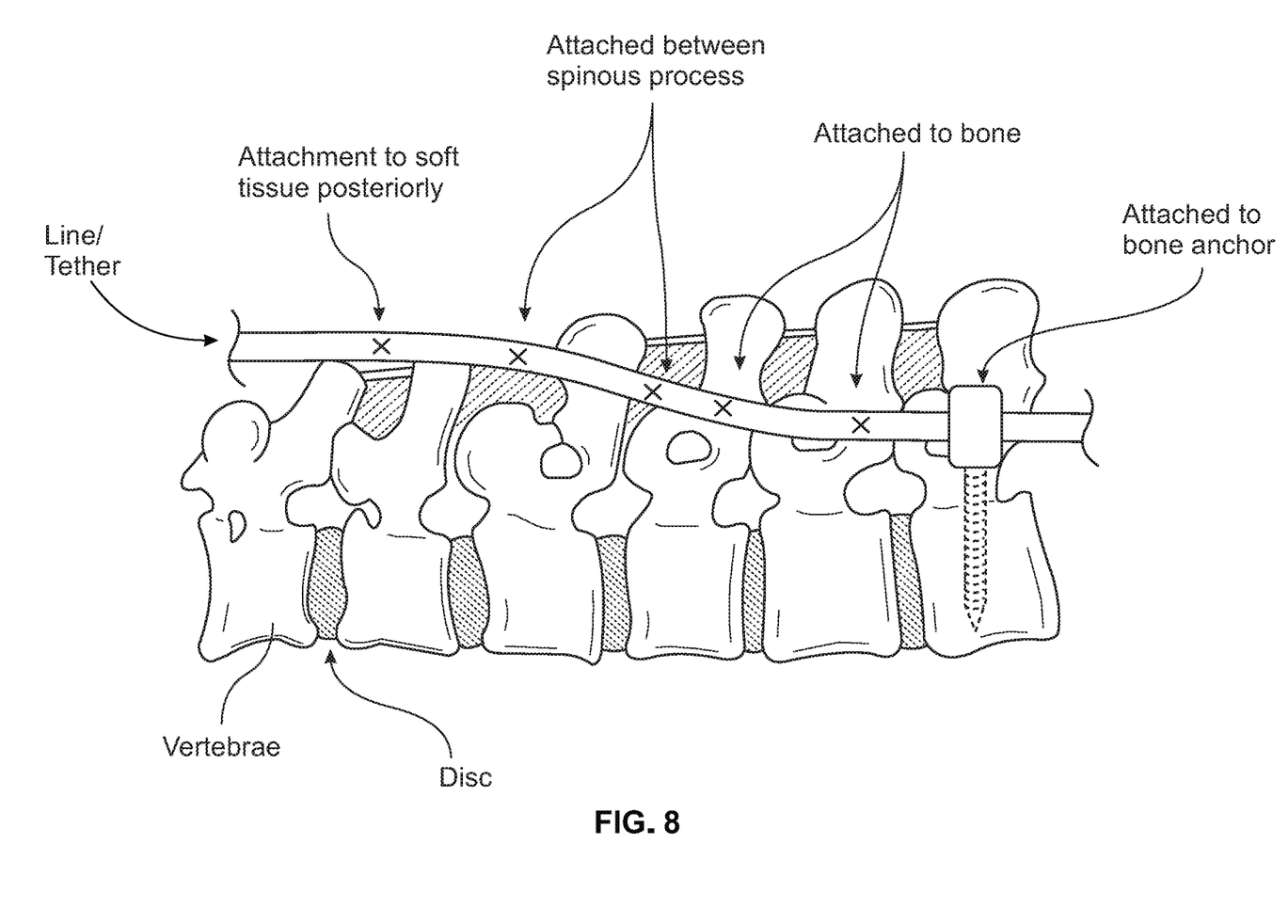
FIG. 8 shows a diagram of an embodiment of a spine having a line or a tether installed thereon in accordance with this disclosure.

FIG. 8 shows a diagram of an embodiment of a spine having a line or a tether installed thereon in accordance with this disclosure. In particular, based on disclosure of FIGS. 1-7, this diagram shows a spine that has a set of vertebrae and a set of discs. The spine has a line or a tether coupled thereto, as disclosed herein. The line or the tether can be attached (or otherwise coupled) to a soft tissue posteriorly, as disclosed herein. The line or the tether can be attached (or otherwise coupled) between a set of spinous processes, as disclosed herein. The line or the tether can be attached (or otherwise coupled) to a bone, as disclosed herein. The line or the tether can be attached (or otherwise coupled) to an anchor, as disclosed herein. Note that all of such forms of attachment can be mixed and matched in any permutational combinatory manner, as disclosed herein. For example, the line or the tether can be attached via one of such methods, at least two of such methods, at least three of such methods, or more or none of any one of such points within human body.

Features described with respect to certain embodiments may be combined in or with various some embodiments in any permutational or combinatory manner. Different aspects or elements of example embodiments, as disclosed herein, may be combined in a similar manner.

Although the terms first, second, can be used herein to describe various elements, components, regions, layers, or sections, these elements, components, regions, layers, or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Features described with respect to certain example embodiments can be combined and sub-combined in or with various other example embodiments. Also, different aspects or elements of example embodiments, as disclosed herein, can be combined and sub-combined in a similar manner as well. Further, some example embodiments, whether individually or collectively, can be components of a larger system, wherein other procedures can take precedence over or otherwise modify their application. Additionally, a number of steps can be required before, after, or concurrently with example embodiments, as disclosed herein. Note that any or all methods or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques or tolerances, are to be expected. Thus, various example embodiments of this disclosure should not be construed as necessarily limited to various particular shapes of regions illustrated herein, but are to include deviations in shapes that result, for example, from manufacturing.

Any or all elements, as disclosed herein, can be formed from a same, structurally continuous piece, such as being unitary, or be separately manufactured or connected, such as being an assembly or modules. Any or all elements, as disclosed herein, can be manufactured via any manufacturing processes, whether additive manufacturing, subtractive manufacturing, or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable others of ordinary skill in a pertinent art to understand this disclosure for various embodiments with various modifications as are suited to a particular use contemplated.

This detailed description has been presented for various purposes of illustration and description, but is not intended to be fully exhaustive or limited to this disclosure in various forms disclosed. Many modifications and variations in techniques and structures will be apparent to those of ordinary skill in an art without departing from a scope and spirit of this disclosure as set forth in various claims that follow. Accordingly, such modifications and variations are contemplated as being a part of this disclosure. A scope of this disclosure is defined by various claims, which include known equivalents and unforeseeable equivalents at a time of filing of this disclosure.

The invention claimed is:

1. A device comprising:
   a first anchor configured to be directly coupled to a first soft tissue in proximity to a first vertebrae of the spine;
   a second anchor configured to be coupled to at least one of a second vertebrae of the spine or a second soft tissue in proximity to the second vertebrae of the spine;
   a line spanning between and coupled to the first anchor and the second anchor, wherein the line is configured to extend past a third vertebrae located between the first soft tissue and the at least one of the second vertebrae or the second soft tissue, and wherein there is no anchor positioned between the first anchor and the second anchor; and
   a protective member encasing the line such that the line is movable relative to the protective member between the first anchor and the second anchor.

2. The device of claim 1, wherein the protective member at least one of
   is coupled to at least one of the first anchor or the second anchor,
   spans between the first anchor and the second anchor,
   is configured for coupling to the first soft tissue or at least one of the second vertebrae or the second soft tissue,
   is configured for coupling to the third vertebrae,
   extends across a sagittal plane,
   does not extend across a sagittal plane,
   is configured for coupling to a hard tissue.

3. The device of claim 1, wherein at least one of the first anchor or the second anchor includes at least one of a fixation device, a hook, a screw, a wire, an anchor, a dart, or a loop.

4. The device of claim 1, wherein the line at least one of is flat, is cylindrical, is synthetic, is elastic, is rigid, includes an autograft, includes an allograft, or is at least one of woven or braided.

5. The device of claim 1, further comprising:
   A compound positioned over the protective member and configured for positioning over and adhering to at least one of the first vertebrae, the second vertebrae, or the third vertebrae of the spine such that the protective member is configured for directly coupling to at least one of the first vertebrae, the second vertebrae, or the third vertebrae via the compound.

6. The device of claim 1, wherein at least one of the first soft tissue or the second soft tissue is at least one of a fibrous tissue, a tendon, a ligament, a cartilage, or a muscle.

7. The device of claim 1, further comprising a third anchor, wherein the line is not affixed to the third anchor.

8. The device of claim 1, further comprising a third anchor, wherein the line is movable relative to the third anchor.

9. The device of claim 1, wherein the protective member at least one of
   includes at least one of a tube, a sleeve, a partial cylinder, or a trough encasing the line,
   has a cross section that is at least one of circular, oval, arcuate, V-shaped, U-shaped, J-shaped, D-shaped, C-shaped, semicircular, curved, or flat,
   is at least one of solid, semi-solid, permeable, or semi-permeable,
   is at least one of rigid, semi-rigid, flexible, or elastic, or
   is tubular.

10. A device comprising:
    a first soft tissue anchor, comprising at least one of a hook, a screw, an anchor, a dart, a suture, a suture tie, an adhesive, a staple, or a tissue bond;
    a second anchor; and
    a flexible, non-rigid line spanning between the first soft tissue anchor and the second anchor, wherein the first soft tissue anchor is configured for coupling the line to a first soft tissue in proximity to a first vertebrae of the spine, wherein the second anchor is configured for coupling the line to at least one of a second vertebrae of the spine or a second soft tissue in proximity to the second vertebrae of the spine, wherein the line is configured to extend past a third vertebrae located between the first soft tissue and at least one of the second vertebrae or the second soft tissue, and wherein there is no anchor positioned between the first soft tissue anchor and the second anchor.

11. The device of claim 10, further comprising a tensioner coupled to the line, wherein the tensioner modifies at least one of a position, a displacement, or a length of the line.

12. The device of claim 11, wherein at least one of the first soft tissue anchor or the second anchor hosts the tensioner.

13. The device of claim 11, wherein the tensioner at least one of
    is manually activated, is automatically activated, or is activated via at least one of a magnetic force, an electrical force, a chemical force, or a mechanical force.

14. The device of claim 11, wherein the tensioner is configured for positioning or activation at least one of internal or external to the body.

15. The device of claim 11, wherein the tensioner includes at least one of a pulley, a winch, a spring, a memory metal, a deforming metal, a mechanical movement, a gear, a ratchet, or a motor.

16. The device of claim 10, wherein at least one of the first soft tissue or the second soft tissue is at least one of a fibrous tissue, a tendon, a ligament, a cartilage, or a muscle.

17. The device of claim 10, wherein the first soft tissue and the second soft tissue are at least one of a fibrous tissue, a tendon, a ligament, a cartilage, or a muscle.

18. The device of claim 10, wherein the line at least one of bends, flexes, or is displaced without actually extending or retracting.

19. The device of claim 10, wherein the line comprises at least one of a tether, a cable, a chain, a wire, a rope, a belt, a band, a braid, a tube, a cylinder, or an allograft.

20. A device comprising:
a line configured for coupling to at least one of a first vertebrae of a spine or a first tissue in proximity to the first vertebrae of the spine, and at least one of a second vertebrae of the spine or a second tissue in proximity to the second vertebrae of the spine; and
a shape retaining moldable compound configured for positioning over the line and configured for positioning over and adhering to at least one of the first vertebrae or the first tissue, the second vertebrae or the second tissue, or a third vertebrae of the spine such that the line is at least one of fixed or movable within the compound relative to the compound and the at least one of the first vertebrae or the first tissue, the second vertebrae or the second tissue, or the third vertebrae, wherein the third vertebrae is positioned between at least one of the first vertebrae or the first tissue and at least one of the second vertebrae or the second tissue, and wherein the compound is directly coupled to at least one of the first vertebrae or the first tissue or to at least one of the second vertebrae or the second tissue.

21. The device of claim 20, wherein the line includes a portion coupled to a tensioner configured for maintaining at least one of a predetermined tension on the line, or a predetermined force on the line such that the line creates at least one of a tension or a displacement between at least two vertebrae of the spine.

22. The device of claim 21, wherein the tensioner at least one of is manually activated, is automatically activated, is activated via at least one of a magnetic force, an electrical force, a chemical force, or a mechanical force, or includes at least one of a pulley, a winch, a spring, a memory metal, a deforming metal, a mechanical movement, a gear, a ratchet, or a motor.

23. The device of claim 22, further comprising a protective member encasing the line.

24. The device of claim 23, wherein the protective member at least one of
is coupled to at least one of the first anchor or the second anchor,
spans between the first anchor and the second anchor,
is configured for coupling to at least one of the first vertebrae or the first tissue or the second vertebrae or the second tissue, is configured for coupling to the third vertebrae,
is configured for coupling to a hard tissue,
contacts the line,
is tubular,
extends across a sagittal plane, or
does not extend across a sagittal plane.

25. The device of claim 23, wherein the protective member includes at least one of a tube, a sleeve, a partial cylinder, a trough, a circular cross section, an oval cross section, an arcuate cross section, a V-shaped cross section, a U-shaped cross section, a J-shaped cross section, a D-shaped cross section, a C-shaped cross section, a semicircular cross section, a curved cross section, a flat cross section, a solid material, semi-solid material, permeable material, semi-permeable material, a rigid material, a semi-rigid material, a flexible material, or an elastic material.

26. The device of claim 21, wherein the tensioner is configured for adjustment to modify at least one of the predetermined tension or the predetermined force.

27. The device of claim 20, wherein at least one of the first tissue or the second tissue is at least one of a fibrous tissue, a tendon, a ligament, a cartilage, or a muscle.

28. The device of claim 20, wherein the compound is curable after positioning over the line.

29. The device of claim 20, wherein the line is flat, is cylindrical, is synthetic, is elastic, is rigid, is woven, includes an autograft, includes an allograft, extends across a sagittal plane, or does not extends across a sagittal plane.

30. A device comprising:
a flexible, non-rigid line;
a first soft tissue anchor, comprising at least one of a hook, a screw, an anchor, a dart, a suture, a suture tie, an adhesive, a staple, or a tissue bond, wherein the first soft tissue anchor is configured for coupling the line to a first soft tissue in proximity to a first vertebrae of the spine;
a second anchor configured for coupling to a second vertebrae of the spine or a second soft tissue in proximity to the second vertebrae of the spine,
wherein the line spans between the first soft tissue anchor and the second anchor, wherein the line extends past a third vertebrae located between the first soft tissue and at least one of the second vertebrae or the second soft tissue; and
a guide configured for coupling to the third vertebrae or a third soft tissue in proximity to the third vertebrae, wherein the guide guides the line, wherein the line is movable relative to the first soft tissue anchor and the second anchor.

31. The device of claim 30, wherein the guide at least one of
applies a constraint to the line, wherein the line is movable based on the constraint,
directs a displacement of the line relative to the first soft tissue, or at least one of the second vertebrae or the second soft tissue,
reduces an unwanted displacement of the line relative to the first soft tissue, or at least one of the second vertebrae or the second soft tissue.

32. The device of claim 30, further comprising a shape retaining moldable compound configured for positioned over the line and adhering to at least one of the first vertebrae, the second vertebrae, the third vertebrae, the first soft tissue, or the second soft tissue.

33. The device of claim 32, wherein the compound is curable after positioning over the line.

34. The device of claim 30, wherein at least one of the first soft tissue or the second soft tissue is at least one of a fibrous tissue, a tendon, a ligament, a cartilage, or a muscle.

* * * * *